United States Patent [19]

Allen et al.

[11] Patent Number: 5,312,925

[45] Date of Patent: May 17, 1994

[54] MONOHYDRATE OF 5-(2-(4-(1,2-BENZISOTHIAZOL-3-YL)-1-PIPERAZINYL)-ETHYL)-6-CHLORO-1,3-DIHYDRO-2H-INDOL-2-ONE-HYDROCHLORIDE

[75] Inventors: Douglas J. M. Allen, New London; Frank R. Busch, Gales Ferry; Sabeto A. DiRoma, Uncasville; Dennis M. Godek, Glastonbury, all of Conn.

[73] Assignee: Pfizer Inc., New York, N.Y.

[21] Appl. No.: 939,204

[22] Filed: Sep. 1, 1992

[51] Int. Cl.$^5$ ............................................. C07D 417/14
[52] U.S. Cl. .................................................. 544/368
[58] Field of Search ......................... 544/368; 514/254

[56] References Cited

U.S. PATENT DOCUMENTS 4,831,031  5/1989  Lowe, III et al. ................. 544/368

*Primary Examiner*—Cecilia Tsang
*Attorney, Agent, or Firm*—Peter C. Richardson; Paul H. Ginsburg; Gezina Holtrust

[57] ABSTRACT

The monohydrate of 5-(2-(4-(1,2-benzisothiazol-3-yl)-1-piperazinyl)ethyl)-6-chloro-1,3-dihydro-2H-indole-2-one hydrochloride has advantageous stability for formulation as a neuroleptic agent.

4 Claims, 6 Drawing Sheets

MONOHYDRATE OF 5-(2-(4-(1,2-BENZISOTHIAZOL-3-YL)-1-PIPERAZINYL)-ETHYL)-6-CHLORO-1,3-DIHYDRO-2H-INDOL-2-ONE-HYDROCHLORIDE

BACKGROUND OF THE INVENTION

The invention is directed to a novel monohydrate of 5-(2-(4-(1,2-benzisothiazol-3-yl)-1-piperazinyl)ethyl)-6-chloro-1,3-dihydro-2H-indol-2-one hydrochloride, a pharmaceutical composition containing said monohydrate and a method of administering said monohydrate to treat neuroleptic diseases.

U.S. Pat. No. 4,831,031 which is incorporated herein by reference, discloses 5-(2-(4-(1,2-benzisothiazol-3-yl)-piperazinyl)ethyl)-6-chloro-1,3-dihydro-2H-indol-2-one hydrochloride of the formula

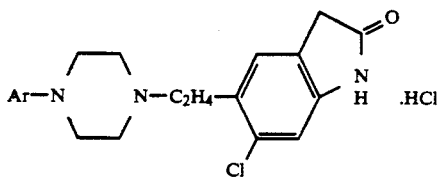

wherein Ar is benzisothiazol-3-yl, in the hemihydrate form (hereafter "the hemihydrate"), having neuroleptic activity.

SUMMARY OF THE INVENTION

The invention relates to the monohydrate of 5-(2-(4-(1,2-benzisothiazol-3-yl)-1-piperazinyl)ethyl)-6-chloro-1,3-dihydro-2H-indol-2-one hydrochloride (hereafter "the monohydrate") which possesses valuable and nonobvious properties. Since the monohydrate is substantially hygroscopically stable, formulation problems due to weight changes of the active ingredient during tabletting or capsulation operations are alleviated.

DETAILED DESCRIPTION OF THE INVENTION

The theoretical water content of the monohydrate is 3.85% by weight. Within the context of the invention, the water content of the monohydrate ranges from about 3.8 to about 4.5% by weight.

Figure 1:
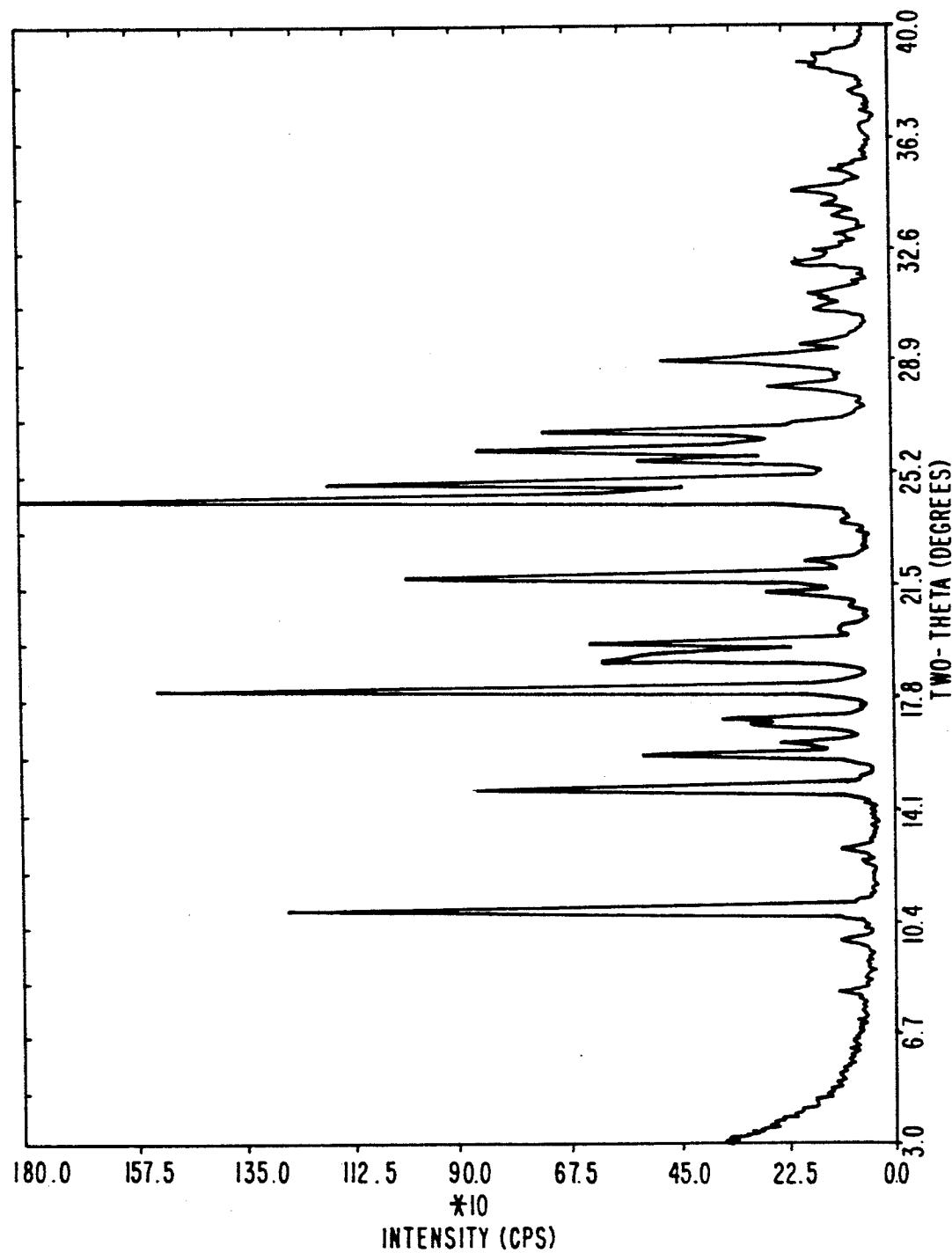
FIG. 1 shows the powder x-ray diffraction of the monohydrate having a water content of 3.97% by weight.
Figure 2:
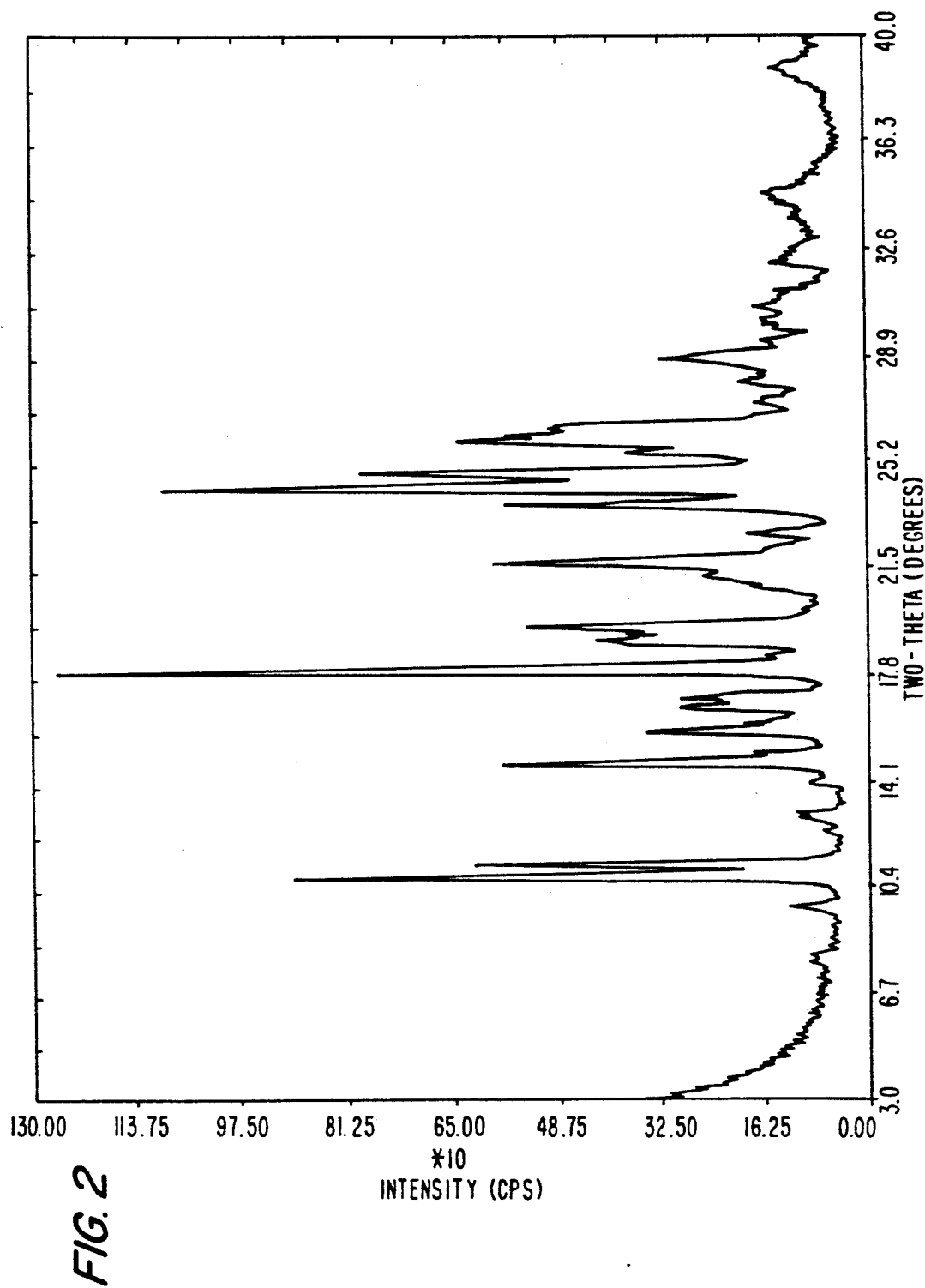
FIG. 2 shows the powder x-ray diffraction of the hemihydrate having a water content of 2.55% by weight.
Figure 3:
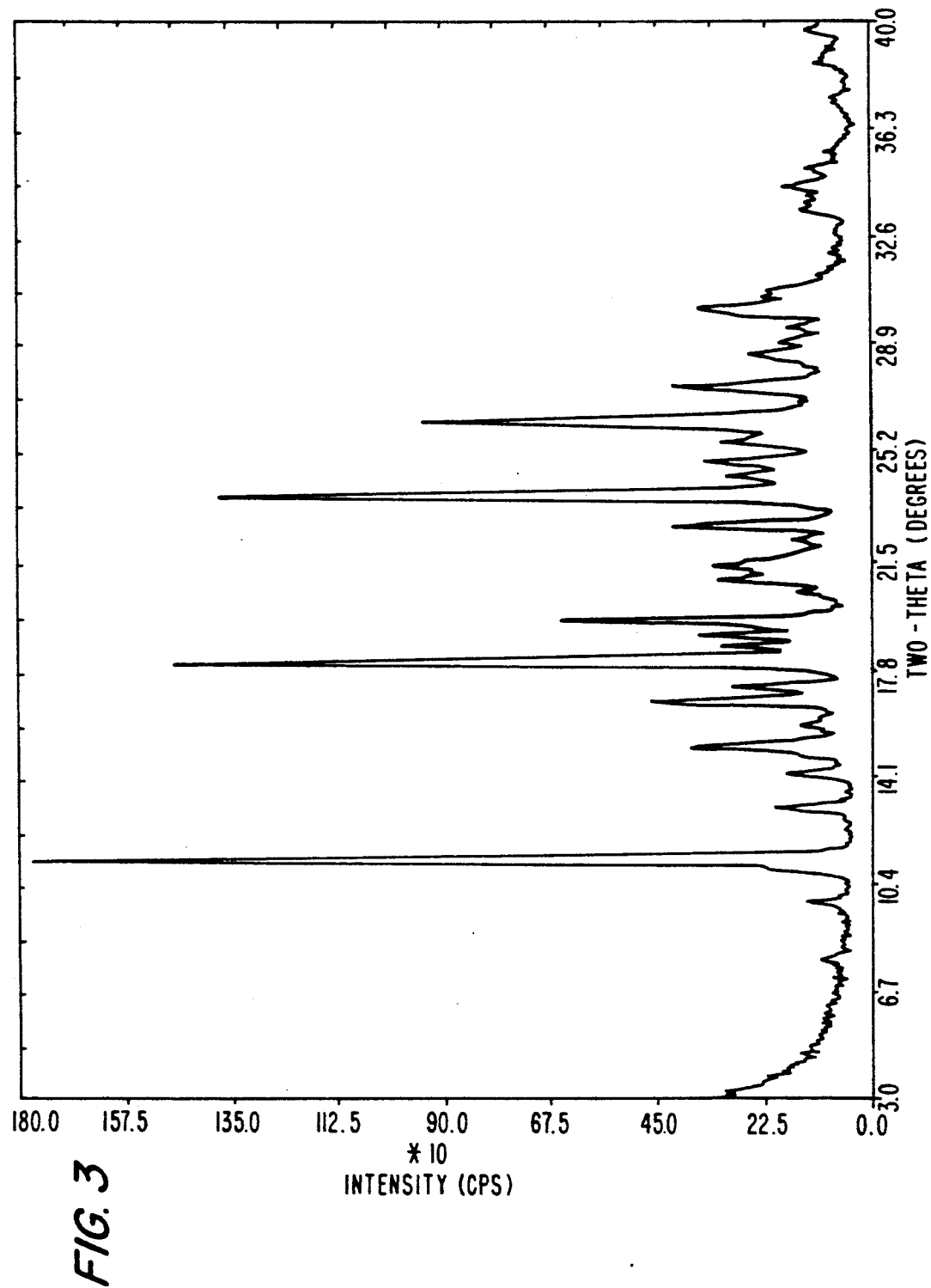
FIG. 3 shows the powder x-ray diffraction of anhydrous 5-(2-(4-(1,2-benzisothiazol-3-yl)-1-piperazinyl)ethyl)-6-chloro-1,3-dihydro-2H-indol-2-one hydrochloride (hereafter "the anhydrous compound") having a water content of 0.13% by weight.
Figure 4:
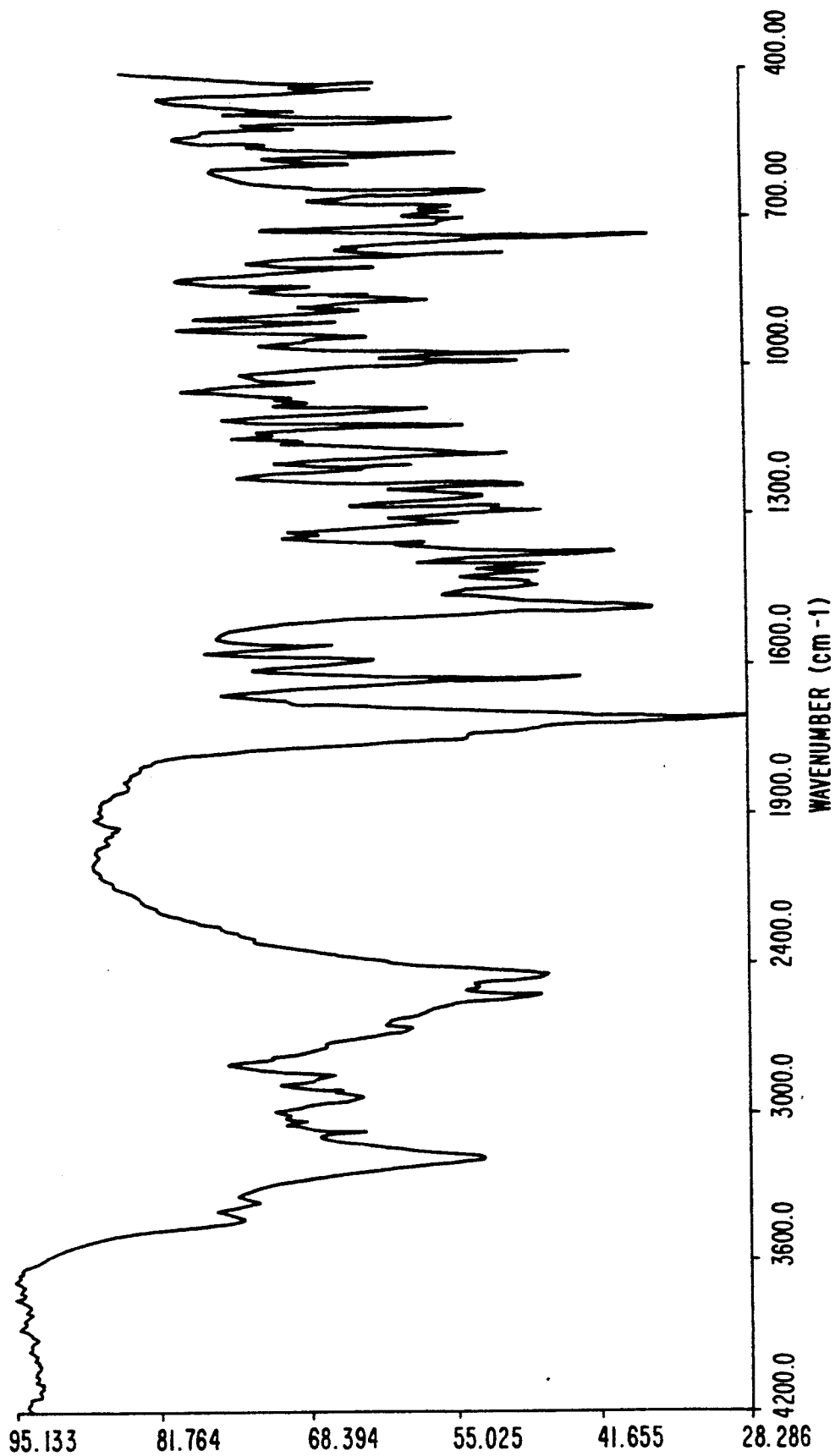
FIG. 4 shows the infrared spectrum of the monohydrate having a water content of 3.97% by weight.
Figure 5:
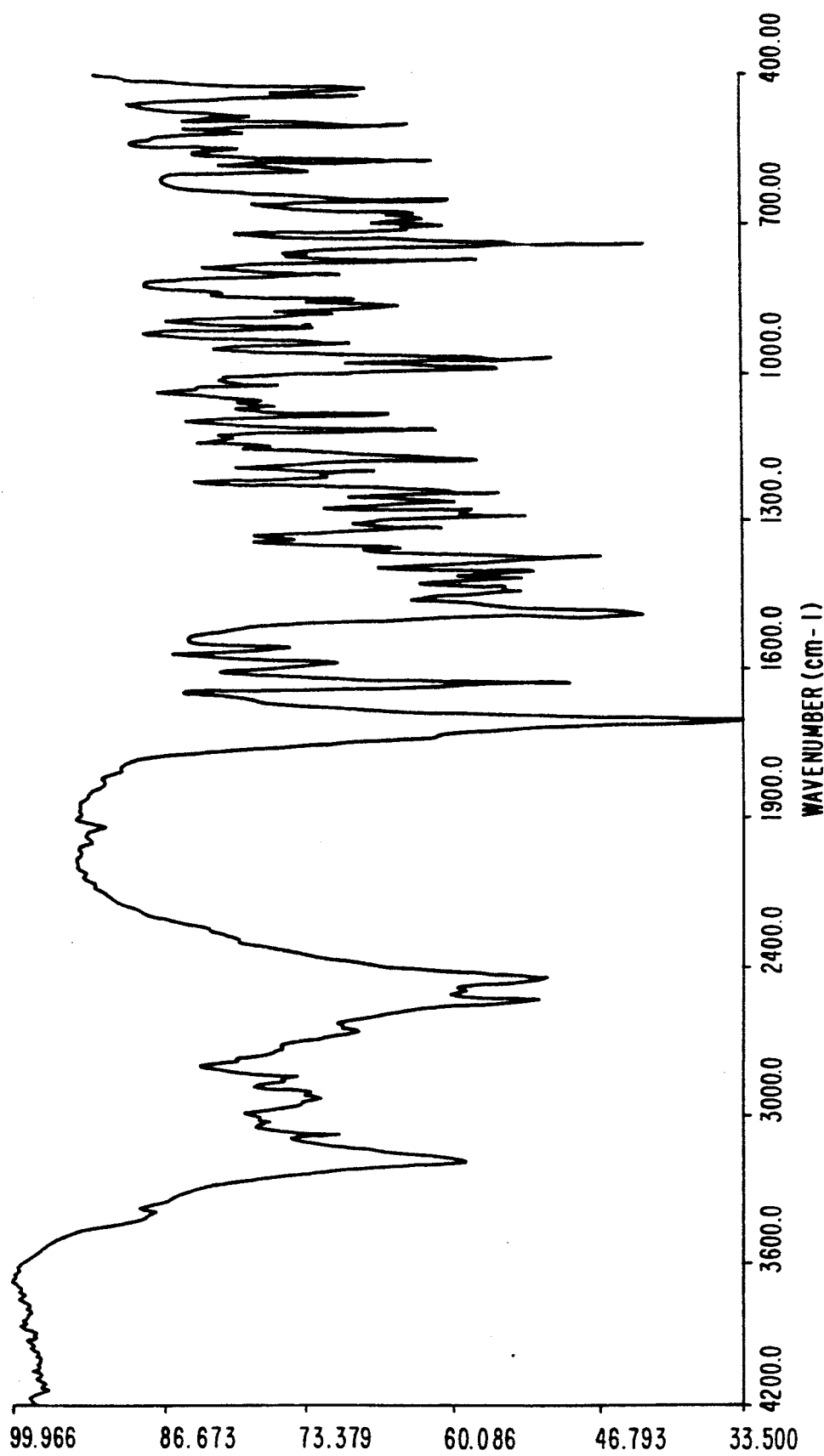
FIG. 5 shows the infrared spectrum of the hemihydrate having a water content of 2.55% by weight.
Figure 6:
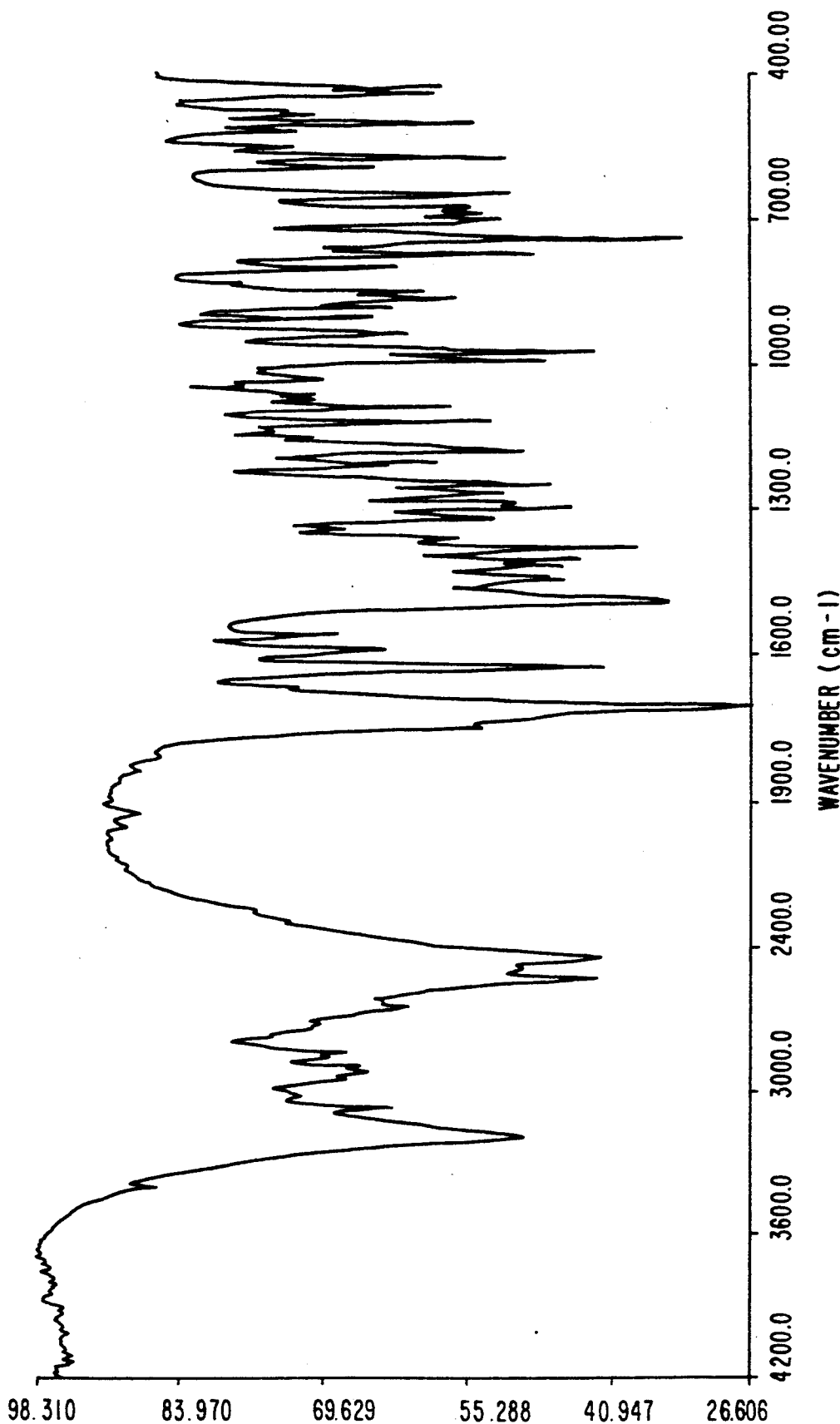
FIG. 6 shows the infrared spectrum of the anhydrous compound having a water content of 0.13% by weight.

The monohydrate is characterized by its water contents its powder x-ray diffraction in FIG. 1 and its infrared spectrum in FIG. 4. These three characteristics are distinct from those of the anhydrous compound having a water content of about 0.13% the powder x-ray diffraction in FIG. 3, and the infrared spectrum in FIG 6. The anhydrous compound may be obtained by drying the hemihydrate or monohydrate compound. The three characteristics are also distinct from those of the hemihydrate having a water content of about 2.55% by weight, the powder x-ray diffraction in FIG. 2, and the infrared spectrum in FIG. 5. The hemihydrate may be obtained by the process described in Example 16, column 13, lines 13 to 17 of U.S. Pat. No. 4,831,031.

The monohydrate may be prepared by reacting anhydrous 5-(2-(4-(1,2-benzisothiazol-3-yl)-1-piperazinyl)ethyl)-6-chloro-1,3-dihydro-2H-indol-2-one with aqueous hydrochloric acid. In general, this reaction takes place at temperatures of from about room temperature to about 100° C., usually from about 60° to about 65° C. Depending on the reaction temperature and other conditions, the reaction time generally ranges from about 2 hours to about 48 hours, conveniently about 3 to 24 hours.

The concentration of the hydrochloric acid in the reaction solution ranges from about 0.3 to about 3.0 M, and preferably about 0.7 M.

The hot slurry formed after reaction may be filtered over paper and the cake washed with water, preferably deionized ultrafiltered water. The cake is dried under carefully monitored conditions to make certain that the water content is from about 3.8% to about 4.5% to obtain the stable monohydrate.

The present monohydrate may be administered as a neuroleptic agent as described in above-mentioned U.S. Pat. No. 4,831,031. Administration to a human subject may be alone or, preferably, in combination with pharmaceutically acceptable carriers or diluents in a pharmaceutical composition, in accordance with standard pharmaceutical practice. The monohydrate may be administered orally or parenterally including intravenously or intramuscularly. Suitable pharmaceutical carriers include solid diluents or fillers, and sterile aqueous solutions and various organic solvents. The pharmaceutical compositions are then readily administered in a variety of dosage forms, such as tablets, powders, lozenges, syrups, and injectable solutions. These pharmaceutical compositions, if desired, may contain additional ingredients such as flavorings, binders and excipients. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solution or suspension of the novel compound of formula I in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

The effective dosage for the compound of formula I depends on the intended route of administration and other factors such as age and weight of the subject, as generally known.

Stability is tested by exposing test samples to relative humidity conditions of 51%, 71% and 81% at room temperature for 4 hours and for eight days. The water contents, infrared spectra and x-ray diffraction patterns are run on each sample. A stable test sample does not show substantial changes under the described conditions.

EXAMPLE 1

A clean 2 L three-neck round bottom flask was made speck-free by rinsing twice with deionized ultrafiltered water, and fitted with a thermometer, mechanical stirrer, reflux condenser and heating mantle. To the flask was added 750 ml of deionized ultrafiltered water, 250 ml concentrated (37.3%) hydrochloric acid, making 3 M aqueous hydrochloric acid, and 50 g of anhydrous 5-(2-(4-(1,2-benzisothiazol-3-yl)-1-piperazinyl)ethyl)-6-chloro-1,3-dihydro-2H-indol-2-one. This reaction mixture was heated to 60° to 65° C. for 24 hours. The slurry was filtered while hot (about 55° C.) over paper, and the cake washed twice with 200 ml each of deionized ultrafiltered water. After drying in air at 40° to 50° C. for 7 hours, the water content was 3.9%. The powder x-ray diffraction was as shown in FIG. 1.

After continued drying for an additional 21.5 hours at 50° C., the water content of the material was 0.19% and the x-ray diffraction was as shown in FIG. 3. Thus, the anhydrous compound was obtained.

EXAMPLE 2

A clean 150 ml three-necked round bottom flask was fitted with a thermometer, magnetic stirrer, reflux condenser with nitrogen inlet, and a heating bath. To the flask was added 5.00 grams of anhydrous 5-(2-(4-(1,2 benieisothiazol-3-yl)-1-piperazinyl)ethyl)-6-chloro-1,3-dihydro-2H-Indol-2-one free base, 75 mi of deionized water, and 5.0 mi of concentrated (37.3%) hydrochloride acid; making 0.76 M HCl solution. This reaction mixture was heated to 60° to 65° C. and held at that temperature for 3 hours. The heating bath was removed and the slurry cooled to room temperature. The product was collected by filtration on a sintered glass filter. The product cake was washed with a small portion of deionized water and then air dried at 50° C. After drying, the water content was 4.2% and the x-ray diffraction pattern matched that shown in FIG. 1. The monohydrate was obtained in 96% yield (5.43 grams).

EXAMPLE 3

A clean and dry 20-gallon reactor was charged with 17.4 gallons of deionized water and 4.44 L of concentrated hydrochloric acid, to give a 0.77 M solution. To the solution was added 4.44 Kg of the anhydrous 5-(2-(4-(1,2-benzisothiazol-yl)-1-piperazinyl)-ethyl)-6-chloro-1,3-dihydro-2H-indol-2-one free base. The slurry was warmed to 65° C. and held for 18 hours. The slurry was cooled to room temperature and sampled; the sample showed that sat formation was complete. The product was filtered and washed with two 5-gallon portions of deionized water, and then air dried at 50° C. for 30 hours. The dried product contained 4.4% water and the x-ray diffraction pattern matched that shown in FIG. 1, confirming that the desired monohydrate was obtained.

The anhydrous free base used in the above Examples was prepared as follows.

EXPERIMENT 5-(2-(4-(1,2-benzisothiazol-3-yl)-piperazinyl)ethyl)-6-chloro-1,3-dihydro-2H-indol-2-one A clean and dry 20-gallon glass lined tank was charged with 19 L of water and 4.44 Kg of sodium carbonate, after the carbonate had dissolved 4.29 Kg (17.5 moles) of 5-(2-chloroethyl)-6-chloro-oxindole and 3.62 Kg (1 6.5 moles) of 1-(1,2-benzisothiazol-3-yl) piperazine were added. The aqueous slurry was heated to reflux and the temperature maintained for 14 hours. When the reaction was complete the solution was cooled to 20° C. and filtered. The wet product was reslurried in 23 L of isopropyl alcohol at room temperature for 2 hours. The product was collected by filtration on 2 large Büchner funnels, each was washed with 3.4 L of fresh isopropyl alcohol. The product was vacuum dried at 30° to 40° C. until no isopropyl alcohol remained, giving 5.89 Kg (86.4% yield) of the desired free base which matched a standard sample by high performance liquid chromatography (HPLC).

We claim:

1. 5-(2-(4-(1,2-Benzisothiazol-3-yl)-1-piperazinyl)ethyl)-6-chloro-1,3-dihydro-2H-indol-2-one hydrochloride monohydrate.

2. A pharmaceutical composition having neuroleptic activity comprising the compound according to claim 1 in an amount effective in the treatment of neuroleptic diseases, and a pharmaceutically acceptable carrier.

3. A method of treating neuroleptic diseases which comprises administering to a subject in need of treatment a neuroleptic amount of the compound according to claim 1.

4. A process for preparing the compound according to claim 1, which comprises reacting anhydrous 5-(2-(4-1,2-benzisothiazol-3-yl)-1-piperazinyl)ethyl)-6-chloro-1,3-dihydro-2-H-indol-2-one with aqueous hydrochloric acid, wherein the concentration of the hydrochloric acid in the reaction solution is about 0.7 M.

* * * * *